US011426050B2

(12) United States Patent
Frankel (10) Patent No.: US 11,426,050 B2
(45) Date of Patent: Aug. 30, 2022

(54) WATER BOIL CLEANING DEVICE (71) Applicant: Noel Frankel, New York, NY (US)

(72) Inventor: Noel Frankel, New York, NY (US)

( * ) Notice: Subject to any disclaimer, the term of this patent is extended or adjusted under 35 U.S.C. 154(b) by 0 days.

(21) Appl. No.: 17/236,078

(22) Filed: Apr. 21, 2021

(65) Prior Publication Data
US 2021/0330173 A1    Oct. 28, 2021

Related U.S. Application Data

(60) Provisional application No. 63/016,733, filed on Apr. 28, 2020.

(51) Int. Cl.
| | |
|---|---|
| *A47L 17/04* | (2006.01) |
| *A46B 11/08* | (2006.01) |
| *A47L 13/22* | (2006.01) |
| *A47L 11/40* | (2006.01) |
| *B05C 1/00* | (2006.01) |

(52) U.S. Cl.
CPC .............. *A47L 17/04* (2013.01); *A46B 11/08* (2013.01); *A47L 11/4083* (2013.01); *A47L 11/4086* (2013.01); *A47L 13/22* (2013.01); *B05C 1/003* (2013.01)

(58) Field of Classification Search
CPC .......... A46B 11/08; A47L 17/04; A47L 13/22; A47L 13/225; A47L 11/4083; A47L 11/4086; B05C 1/003
USPC ........................................ 401/263, 266, 270
See application file for complete search history.

(56) References Cited

U.S. PATENT DOCUMENTS

| | | | |
|---|---|---|---|
| 3,239,960 A | 3/1966 | Stevens | |
| 4,559,665 A | 12/1985 | Fitzwater | |
| 5,237,720 A | 8/1993 | Blase | |
| 5,500,977 A | 3/1996 | McAllise et al. | |
| 5,888,006 A | 3/1999 | Ping | |
| 6,146,040 A * | 11/2000 | Dunn ................... | A46B 11/002 401/123 |
| 6,295,691 B1 | 2/2001 | Chen | |
| 6,425,701 B1 | 7/2002 | Jacobs | |
| 7,008,592 B2 | 3/2006 | Sias | |
| D685,549 S | 2/2013 | Wong | |
| 8,889,081 B2 | 11/2014 | Schwartz et al. | |
| D770,116 S | 10/2016 | Neumann | |
| D777,447 S | 1/2017 | Li | |

(Continued)

*Primary Examiner* — Randall E Chin (57) ABSTRACT

A dispensing handle device is disclosed comprising a handle housing having an internal reservoir in which a water boil is prepared to temperatures that clean and, according to the guidelines of governmental health organizations, effectively disinfect surfaces in a post-pandemic world. Moreover, governmental health organizations caution against potentially harmful "chemical" disinfectants or natural products that may not kill microorganisms and therefore are ineffective. Further, the handle applicator has a passageway through which the water boil is dispensed; and a base plate member having an applicator surface on one side and attachable at an opposite side to the handle housing. Integrally formed with the base plate member is a valve comprising a lever and a plurality of torsion spring members, which pressure a sealing end of the lever against the handle housing, whereby sealing the water boil passageway to discharge the water boil in a controlled manner.

21 Claims, 10 Drawing Sheets

(56) References Cited

U.S. PATENT DOCUMENTS

| | | | |
|---|---|---|---|
| 2008/0034514 A1* | 2/2008 | Rosenzweig | A47L 13/225 15/4 |
| 2010/0088932 A1* | 4/2010 | Rosenzweig | A47L 11/34 38/77.8 |
| 2014/0259510 A1* | 9/2014 | Conrad | A47L 13/225 15/319 |
| 2018/0214586 A1 | 2/2018 | Louis et al. | |
| 2019/0104907 A1* | 4/2019 | Javit | D06F 75/12 |

* cited by examiner

WATER BOIL CLEANING DEVICE

The present Application for Patent claims priority to Provisional Application No. 63/016,733 filed 28 Apr. 2020.

BACKGROUND OF THE INVENTION

The present invention relates to handle cleaning devices in general, and specifically to devices that have a cleaning liquid dispensing handle and a cleaning pad disposed at the end of the handle to receive the cleaning liquid.

A helpful addition to the handle cleaning device is the internal reservoir for storing a liquid cleanser in its handle, which uses gravity to dispense the cleaner into the sponge member at one end. The liquid cleanser can thereby be supplied continuously to any surface which comes in contact with the sponge. The liquid dispensing devices represent an improvement over ordinary handheld devices; however, common cleaning products discharged by these devices may be costly and toxic to human beings, while the environmentally friendly alternatives may not be efficacious enough to deep-clean various surfaces.

A government ruling supports outside researchers who have long argued that chemically-based household disinfectants are potentially harmful and toxic to humans or animals. To assess a possible association between COVID-19 cleaning recommendations and the number of chemical exposures reported to poison centers during January-March 2020, the National Poison Data System (NPDS), CDC, and the American Association of Poison Control Centers received 45,550 exposure calls related to commercial cleaners. In addition, the Food and Drug Administration found that sanitizing agents in myriad kitchen and bathroom cleaning products can interfere with hormone levels in lab animals and spur the growth of drug-resistant bacteria, while popular household remedies, such as white vinegar and apple cider vinegar, are ineffective against coronavirus and its rapidly emerging highly contagious variant strains.

Small children around the house are a constant reminder of the toxicity of most common cleaning products. In contrast, "green" cleaning products command a higher price point but may not be as effective as the "chemical" brands. Further, research shows that household cleaning products available in the U.S. could contain compounds banned in other countries known to cause blindness, cancer, asthma, and other severe conditions. Today, liquid cleaning products routinely vie for market share through competitive claims. However, claims that designate products as environmentally preferable are not necessarily subject to objective standards or regulatory bodies. Products labeled "natural" may contain chemicals that are hazardous to human health.

Any discussion of the prior art throughout the specification should in no way be considered as an admission that such prior art is widely known or forms part of the common general knowledge in the field. Apart from handle devices designed to wash dishes and clean household surfaces and the present invention, which accomplishes these tasks while specifically killing or inactivating pathogens, viruses, bacteria, protozoa, and fungi, there are patented devices that may appear to perform such functions adequately. However, upon closer examination, they are more expensive to manufacture, may not accomplish the same tasks, or provide for ease of operation by the user. For example, electric foggers and similar apparatus, under patents U.S. Pat. Nos. 3,239,960A, 7,008,592, 10,111,974, 8,889,081B2, US20180214586A1, may include a housing having a heat source, a timer, and a disposable canister containing a fog-producing material such as an insecticide, deodorant, perfume, disinfectant or air freshener. However, according to the World Health Organization (WHO), in indoor spaces, applying disinfectants to surfaces via spraying is not recommended for viruses such as Covid-19. Disinfectants should be applied with a cloth or wipe, soaked in the disinfectant, the WHO advises. Moreover, the guidance adds, spraying disinfectants can result in risks to the eyes, respiratory or skin irritation. In non-healthcare settings, such as "environmental surfaces," including dishware, sinks and toilets, electronic devices (touch screens and controls), furniture and other fixed items like countertops, stairway rails, floors, walls, door handles, etc., the WHO guidance cautions, in the context of Covid-19, that spraying is ineffective in removing contaminants outside of the direct spray zones, which also applies to many steam cleaners on the market today. For example, a vapor cleaning device, U.S. Pat. No. 6,295,691, includes a boiler in a case that generates steam. The conical or cone-shaped region of steam has the temperature required for cleaning. Still, the cleaning area is limited to the center of the conical bottom, which means the steaming the peripheral portion typically leads to poor performance and may not kill pathogens due to lower steam temperatures. Additionally, the high power requirement for generating steam may not allow ample remaining power for miming a vacuum motor; consequently, steam cleaners are generally inefficient. Handheld garment and fabric steamers remove wrinkles from clothing, small areas on drapes, couches, pet beds, etc. Larger in size, water tank extraction cleaning machines are designed to clean carpeting, upholstery, and drapes, such as U.S. Pat. Nos. 5,500,977 and 4,559,665, or in the form of a canister-type unit, as disclosed in U.S. Pat. No. 5,237,720. In either case, foggers and steam cleaners may use detergents that can be hazardous to human health. Moreover, these devices are typically sold at a far greater price point than handle cleaners and are generally inefficient for the purposes described herein.

Patents for handle dishwashing cleaning devices, among others, include U.S. Pat. No. 5,888,006A, 685,549S1, 777, 447 S, 770,116S1, and 6,425,701B1, which focus on liquid dispensing features without specifying disinfectant capabilities. According to the Food and Drug Administration, the code for dishwashing by hand in a commercial food establishment calls for a wash solution temperature of 110° F. However, even at 110° F., a temperature that is uncomfortably hot for hands, it is still not hot enough to kill pathogens, such as COVID-19. Popular home economic resources also recognize the difficulty in disinfecting dishes washed by hand and advocate a two-stage process that begins with washing the dishes. Then, second, soaking them in a sanitizing solution that kills microorganisms. This information may be more reliable than one might think. About 68 percent of American households have a dishwasher with water that reaches a scalding 140° F., which some research cites is a temperature, at a minimum, that kills most bacteria on a dirty dish but is unavailable from a sink faucet. Moreover, consumer safety concerning cleaning liquids dispensed by the above-named patented devices and these commercial products' cost is not specifically referenced. Generally, except for patent U.S. Pat. No. 6,425,701B1, the discharge of liquid cleansers from handle devices is primarily continuous and unregulated; consequently, more liquid than necessary may be deposited on the sponge, or suitable applicant adds waste which increases the cost of operation. However, U.S. Pat. No. 6,425,701B1 is an improvement over the aforementioned handle cleaning devices, as it controls and conserves the capacity of liquid in the reservoir through a connection between the sponge member and the handle, which is liquid-tight, to eliminate leakage of the fluid. between the components, which conserves the cleaning liquid and reduces cost. Further, the specification for the invention named above stipulates that the subject applicator may be adapted for use in non-cleaning applications, such as liquid adhesives, liquid wax, or controlled fluid flow applications from a reservoir are required, such as the dispensing of a beverage. However, the specification for this device does not include the application of disinfectants to kill pathogens, such as the novel coronavirus, as it washes dishes or cleans household surfaces; nor do the limitations include a means to heat any liquid dispensed by the handle device.

Under USPTO 35 U.S.C. 101, "Whoever invents or discovers any new and useful process, machine, manufacture, or composition of matter, or any new and useful improvement thereof, may obtain a patent, therefore, subject to the conditions and requirements of this title." Unlike the aforementioned patent U.S. Pat. No. 6,425,701B, the present invention adds healthful disinfectant capabilities while significantly reducing operating costs. For example, at room temperature, a liquid, such as water, is commonly given as 68° F., which, correspondingly, would be the same temperature of the cleaning preparations stored at room temperature for use in the above-named handle device. Although tap water could reach a higher temperature than liquids at room temperature, it falls well short of the temperature recommended by governmental agencies and private sector industries to disinfect dishes and household surfaces efficaciously. In respect to new and useful improvements, as outlined in title 35 U.S.C. 101, the advancements of the present invention over patent U.S. Pat. No. 6,425,701B are fourfold: First, the present invention cleans, disinfects, and sanitizes dishes and other household surfaces while it kills pathogens, such as the novel coronavirus. Second, the present invention disinfects without liquid cleaners that, according to the EPA, may contain chemicals that are harmful to humans. Third, it accomplishes household disinfecting and cleaning tasks for significantly less than the cost of commercially marketed liquid cleaners recommended and promoted for use in handle devices. Fourth, one iteration of the present invention is biodegradable; a preferred embodiment that reinforces a positive climate change outcome while explicitly designed for use with a conventional consumer microwave oven. The handle device for use in a microwave scientifically engineered to safely bring water in its reservoir to temperatures that, according to the guidelines of governmental health organizations worldwide, effectively disinfect water boil stable surfaces in a post-pandemic world.

Further, U.S. Pat. No. 6,425,701B I does not ascribe to said governmental guidelines. However, the present invention is engineered to dispense from its reservoir to the sponge member a water boil. This 100% natural liquid kills or inactivates viruses, bacteria, protozoa, fungi, and pathogens, while the handle device of the present invention protects the consumer's hands. Furthermore, the inventive matter of U.S. Pat. No. 6,425,701B I does not differentiate its product usage between cleaners that may be toxic to human beings from the environmentally friendly so-called "green" alternative cleaners that may not be as effective as the chemical brands. Moreover, regardless of the liquid dispensed, U.S. Pat. No. 6,425,701B is not engineered to be microwave-safe. In contrast, the present invention reservoir is constructed of a patent-eligible roughened interior surface that promotes nucleation sites that produce nucleant bubbles. The presence of nucleant bubbles eliminates unintentional super-heating of the water, which has been cited in many scientific journals as unsafe due to the possibility of explosions when boiling water in a microwave oven. Consistent with its eco-friendly commitment, the present invention is primarily an injection-molded biodegradable thermoplastic with a handle grip comprised of a fiber such as silica that protects a user's hands to temperatures of 1800° F. Moreover, traditional handle devices continuously dispense liquid cleaners in unregulated amounts. In contrast, the connection between the sponge member and the handle in the present invention is liquid-tight, eliminating leakage of the water boil between the components to further assure the product's safety. At same time, neither the aforementioned chemical products nor the so-called "green" cleaners are more effective nor economical than the water boil of the present invention, which adds a specific limitation other than what is a well-understood, routine, conventional activity in the realm of handle cleaning devices. Specifically, the present invention will cost-effectively kill bacteria, protozoa, viruses, and other pathogens while it deep-cleans water boil stable surfaces without harmful chemicals, fog, or conical steam. When the inventor considered the patentability of the present invention's improvements over U.S. Pat. No. 6,425,701B, the entire disclosure was reviewed to ascertain meaningful technical differences between the disclosure and improvements exhibited by the present invention. Technical differences, such as the inclusion of nucleation sites in the reservoir of the present invention, which produce nucleant bubbles that safely eliminate the unintentional super-heating of boiling water, is an improvement that has requisite statutory novelty. Moreover, the advantages of an all-natural, unlimited liquid disinfectant supply, as opposed to the scarcity of potentially harmful chemical products, or possibly costly yet ineffective "green" brands, the water boil handle device maintains the highest environmental compliance at the lowest possible price point heretofore, the differences between the improvements and the disclosure are such that one skilled in the art to which the improvements relate would not find the differences obvious when the invention was made. Therefore, the difference is nonobvious, and the improvement is patentable. As described herein, the present invention answers the challenge of environmental cleaning and disinfectant concerns without tying up the judicial exception, as the claims do not wholly pre-empt the field and pose no risk of pre-emption because, as enumerated herein, non-infringing alternatives are significant and substantial.

SUMMARY OF THE INVENTION

While person-to-person transmission of COVED-19 poses a much greater risk than transmission via surfaces, the Centers for Disease Control (CDC) recommends cleaning and disinfecting high-touch surfaces at least once a day, even if homeowners are not leaving the house. Furthermore, a study in Virology Journal (Forbes, 11/2020) showed that the virus can remain active up to 48 hours on stainless steel, linoleum, glass, plastic, and ceramic surfaces. A novel alternative to the cleaning devices mentioned above, the present invention does not depend on inefficient fog or conical stream dispersions, potentially hazardous chemical products, or the questionable performance of so-called "green" options. Instead, the present invention safely boils, stores, and dispenses an effective water boil disinfectant. A preferred embodiment, the water boil is defined, specifically, in regard to the present invention, as a rolling boil of 212° F. to a vigorous simmer/gentle boil at 195° F., followed by a drop to 160° F., all of which, research shows, kills pathogens such as COVID-19. A biodegradable thermometer temperature indicator color-changing display, plainly visible through the transparent water view reservoir window, allows the user to monitor the water temperature, from 212° F. to 160° F. Although studies indicate that 145° F. kills the coronavirus, as a disinfectant safety measure, the present invention instructs the user to refill the reservoir with water when the display indicates 160° F., as this higher temperature falls well within the plurality of guidelines for an effective disinfectant. Further, a visible Fahrenheit scale may display temperatures in increments of 20° F., from a boil at 212° F. to 160° F., as either the electronic or battery-powered models of the present invention may be turned 'on' and 'off,' increasing or decreasing the water temperature throughout the cleaning and disinfection process.

Notably, manufacturers of cleaning products are not required to disclose the ingredients used in their products; subsequently, consumers may be unaware of the potential health hazards. Women's Voices for the Earth (WVE) commissioned an independent laboratory to test twenty popular cleaning products for hidden toxic chemicals from five top companies: Clorox, Procter & Gamble, Reckitt Benckiser, SC Johnson and Son, and Sunshine Makers (Simple Green). WVE found reproductive toxins, carcinogens, hormone disruptors, and allergens, while these chemicals were unfortunately omitted from the manufacturer's product label. Still, as the worldwide coronavirus pandemic spiraled out of control, consumers of Lysol and Clorox, for example, experienced product shortages as substantial increases in production couldn't keep up with demand. In contrast, a lack of water for the present invention seems highly unlikely.

As a cleaning agent, the water boil is enhanced with a preferred embodiment that adds to the reservoir of the present invention, as a user elective, pure liquid biodegradable soap concentrate. For example, castile soap enhances the cleaning and disinfecting experience as it destroys the lipid membrane of the virus, thereby, in combination with the water boil, destroys the virus itself Further, high water boil temperatures cause water molecules to move relatively faster, it will also cause the hydrogen bonds between them to form and break at a higher rate (that is why hot water vaporizes more quickly than cold water). Moreover, the high temperature increases the water's energy and may use this energy to break bonds between dirt and a surface for which colder water will not have enough energy. This means that the detergent/water solution will be able to dissolve (form bonds with) the dirt faster and better because the bonds between the detergent and water and the bonds between the detergent and dirt will form faster and will be strong enough to prevent the dirt from reforming the bonds with common household surfaces. Further, the present invention can effectively and safely clean countertops, wooden furniture, kitchen and bathroom floors, dulled and stained due to the build-up of oils and cleaning products over time.

The specification discloses multiple preferred embodiments to produce the water boil. One such embodiment achieves the water boil externally, in a tea kettle, pan, pot, or similar container, on a stovetop, a hotplate, or any other means. The water boil is then poured into the present invention reservoir through the water intake spout and hole tone assembly. Additional water boil iterations include electricity and battery power, both of which bring water to boil through an immersion heating element in the handle housing reservoir. HydraCell fuel technology, which uses saltwater as a power source to charge cell phones, USB devices, and ambient lighting, may be employed to create the water boil.

By way of example, patents such as EP0748533A1, U.S. Pat. Nos. 3,732,751A, 5,667,029A, and CA2343056C disclose various means of power. A preferred embodiment of the present invention is the nonobviousness of microwaving the handle device in its entirety, in a conventional microwave, which accomplishes a water boil in its reservoir. Undoubtedly, safe microwaving is a prerequisite of the present invention, which provides a reservoir with a roughened interior surface to permit a nucleation site formation, which causes bubbles that eliminate unintentional superheating of the water boil. Currently, nearly 90% of American households have a microwave, according to the US Bureau of Labor Statistics, with the worldwide microwave oven market expected to grow at a compound annual growth rate (CAGR) of roughly 4.5% over the next five years.

The power source notwithstanding, the specification discloses that monitoring the present invention's water boil temperature can be achieved by several methods. A preferred embodiment unknown in the realm of handle cleaning devices employs a thermostat, which is applied practically in modern tea kettles, to automatically switch off the water boiling mechanism by either mechanical, electrical, or electronic means. Another preferred embodiment is the bimetallic thermostat, which integrates with a heating element unit in the reservoir to monitor the water and safely switch off when the water temperature has reached the required cleaning temperature. This embodiment consists of a disc of two different metals bonded tightly together, one of which expands faster than the other as the temperature rises. Normally the thermostat is curved in one direction. However, when the hot water reaches boiling point, the steam produced hits the bimetallic thermostat and makes it suddenly snap and flex in the opposite direction, a bit like an umbrella turning inside out in the wind. When the thermostat snaps open, it pushes a lever that trips the circuit and cuts off the electric current. Another embodiment employs a thermostat inside the reservoir that is entirely electronic, which heats and maintains water to the desired temperature indefinitely by repeatedly switching the current on and off Another preferred Embodiment monitors the water boil utilizing a whistling sound commonly associated with tea kettles fitted with a device that emits an audible whistle when the water in the kettle reaches a boiling point. The action of steam passing through the device causes vibration, which, in turn, creates the sound known in physics as a hole tone. Another embodiment of the present invention is the hole tonesteam escape disc without the tone elements necessary to produce the whistling, as visual steam informs the user that the water temperature has reached the desired cleaning temperature without relying on an audible "tea kettle" alert whistle. Another preferred embodiment calls for the nonobviousness of microwaving the entire handle cleaning device to arrive at a water boil in its reservoir. This product may utilize the whistle's preferred embodiments and the steam, which can be employed separately or in tandem to indicate when the water has reached a boiling point. In sum, the above-named temperature monitoring references are novel and unknown in relation to the present invention. Furthermore, the application of water boil in the realm of handle devices, specifically to disinfect various stable water boil surfaces, would be nonobvious to a person with ordinary skill in the relevant art, as would teaching, suggestion, or motivation to combine the cited references with the prior art.

Regardless of the above-mentioned water temperature monitoring methods, the Steam Safety Shield, another preferred embodiment, presents a visual display of the steam, which releases the energy of boiling water conventionally, thereby preventing an explosion. Moreover, the Shield protects those areas of the arm, primarily the wrist and forearm, from escaping steam throughout the cleaning process accomplished with one hand, such that the other "free" hand can move objects, so that the surface can be wiped clean of residue with a kitchen towel, dishcloth, or wash cloth; or by the appropriate heat-resistant kitchen "oven" mitt, which may be supplied, or purchased separately, as a related item.

Once the user fills the device with tap water and employs the power toggle switch to turn it on, the heating element inside the wand produces water boil, as indicated by the steam, which visibly appears rising through the Safety Shield. The user may choose to clean at a full boil of 212° F., or intermittently shut off the power source to the invention and clean at a vigorous simmer boil, again, indicated by the steady wisps of steam visible through the transparent Shield. A search of the prior art has not stated an application or patented invention that produces water boil, indicated by the present invention, which is defined as either water at a full boil or vigorous simmer/gentle boil, whereas each state is defined as a boil, since each such state remains undiminished in its ability to possess the efficacy to kill pathogens and deep-clean various household surfaces, thereby substantiating the novelty and usefulness of the present invention.

According to another aspect of the present invention, the applying member sponge is releasably engageable with a handle for the device such that the applying member can be replaced as it becomes progressively more soiled after a number of uses. The applying member is designed to enable the water boil to be quickly and evenly dispersed from the dispensing mechanism through the applying member for even application of the water boil to the surface.

Another preferred embodiment, the novel "Steam Safety Shield" allows the user to visually monitor the water boil, as indicted by the steam it produces; protects the user's hand from proximity to the steam during the cleaning process; reduces manufacturing costs as compared to the aforementioned methods to monitor the state of the water boil. However, the specification does not limit the present invention based on one particular embodiment that focuses on the specification. Instead, the specification should be interpreted with respect to its entire disclosure, including any and all embodiments described or mentioned herein.

DETAIL DESCRIPTION OF THE INVENTION

It will be appreciated, that many options are available with respect to the shape of the body and design to be used in association with the present invention and its various iterations. Further, the descriptions of the present invention are not to be taken in a limiting sense, but are made for the purpose of illustrating general principles of the embodiments of the invention.

Figures 1, 2, 2A:
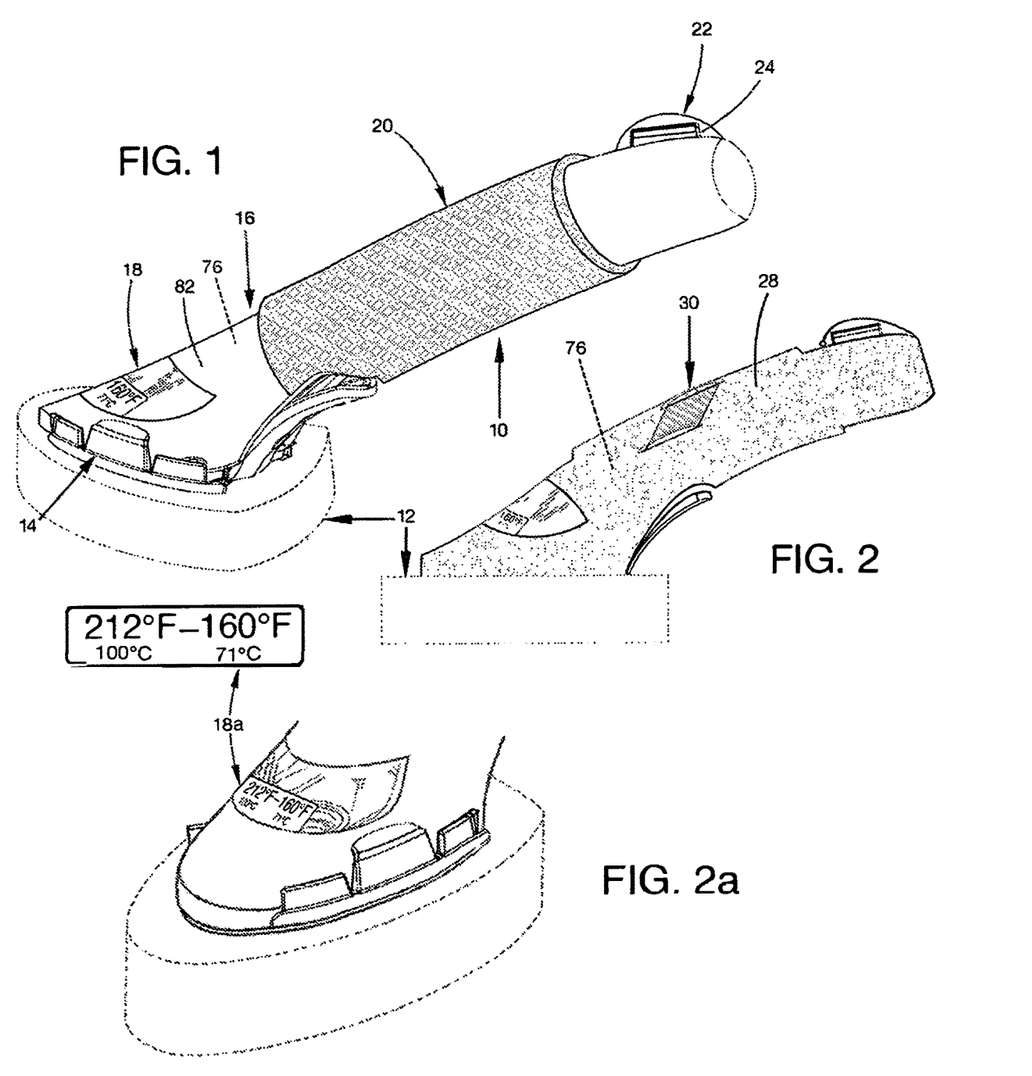
FIG. 1 is a top rear perspective view of the subject microwavable water boil dispensing device.
FIG. 2 is an exploded side view with nucleate interior surface.
FIG. 2a is a top front view of the microwavable water boil dispensing device, with transparent water level view window and the thermometer temperature indicator Color Changing Display.

Referring initially to FIGS. 1, 2 and 2a, the subject dispensing microwavable handle device 10 is seen to comprise an applicator sponge 12, an applicator base plate 14, a handle member 16, a transparent water level view window with the thermometer temperature indicator Color Changing Display 18a, the protective handle grip 20, a transparent steam protective shield 22, and a reservoir spout and steam hole tone 24. The sponge member 12 is a biodegradable natural cellulose, with physical properties that may not be altered up to about 284° F., and an injection molded biodegradable plastic handle device, such as Plastarch, which is a biodegradablethermoplastic and one of few bioplastics capable of withstanding temperatures of 302° F. The baseplate 14 may have a sectional dimension of 0.80 thousandths of an inch relative to the handle member 16 and the water level view window, both of which are on the order of 0.60 thousandths of an inch, which includes the transparency of the water view window 18 irrespective of the body handle 16 which has an opaque colorant. A biodegradable thermometer temperature indicator Color Changing Display 18a is a visual monitor of the water boil temperature in the reservoir, from a boil at 212° F. to 160° F., which kills pathogens, such as Covid-19. Moreover, regardless of the water level visible through the transparent view window 18, when the Color Changing Display registers a temperature of 160° F., the accompanying product guide will advise the user to refill the reservoir and bring the water to a boil before the cleaning and disinfecting process resumes.

While a temperature of 40° F. will kill pathogens, the 20° F. build-in safety buffer assures that the Color Changing Display indication of 60° F. will alert the user to refill well before the water boil cools to an inefficacious level. The protective handle grip 20 is a biodegradable silica fiber that protects the user's hand to temperatures of 1800° F. The transparent steam protective shield 22 and water intake-steam passage spout 24 are the thickness of the above-named handle member 16 and the water level view window 18. As shown in FIG. 2 the exploded interior reservoir view 76 of the microwaveable handle device is formed of roughened plastic to facilitate the nucleate 28; the exploded heat resistant screw threaded pole hole 30 to attach the gripping portion of a foot pole (not shown) to aid mobility of the handle device 16 applicator sponge 12 on surfaces such as floors.

Figure 3:
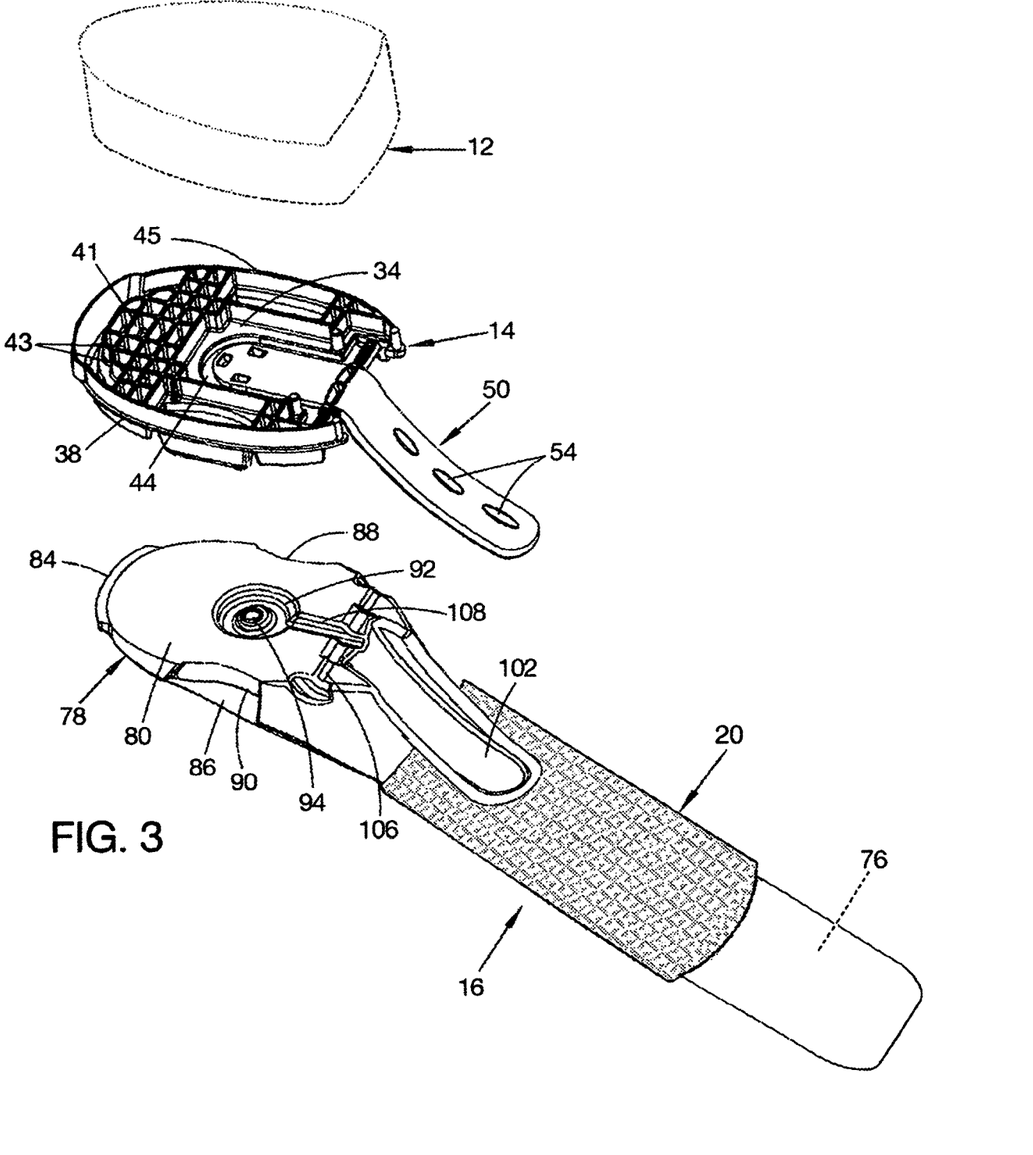
FIG. 3 is an exploded perspective view.
Figure 4:
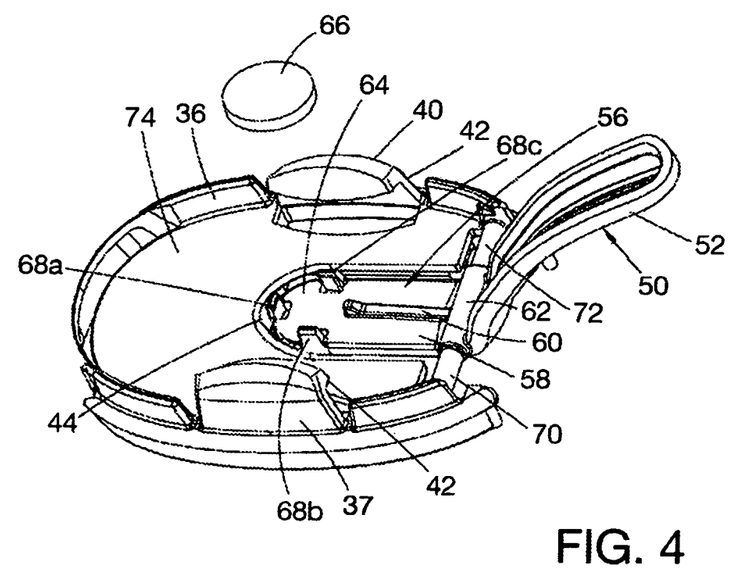
FIG. 4 is an exploded perspective view of the applicator attachment base plate.

As shown in FIGS. 3 and 4, the biodegradable natural cellulose sponge 12. The molded plastic applicator base plate 14 comprises a generally flat plate upper surface 32 of oval shape and a generally flat plate lower surface 34 likewise of oval configuration. An upwardly extending rim flange 36 extends about the perimeter of the plate upper surface 32. A lower skirt 38 extends the perimeter and depends downwardly from an outer edge of the plate lower surface 34. A pair of locking tab projections 37, 40, integrally formed with the base plate 14, project upward in cantilever fashion from opposite sides of the plate upper surface 32. Each locking tab projection 40, 37, provides an inwardly facing sip surface 42. AU-shaped opening 44 extends through the base plate 14 from a rearward edge to a midportion of the plate 14. Within the underside of the base plate 14 is a cavity 46 defined by the plate lower surface 34 and the dependent skirt 38. A matrix of intersecting reinforcement ribs 43 cross the cavity 46, with the lower edge of the ribs 42 being co-planar with a lower edge 45 of skirt 38. An actuation lever 50 is integrally molded with the base plate 14, comprising a rearwardly disposed trigger arm 52. Digit-locating protrusions 54 are paced along an underside of the trigger arm 52. At the forward end of the lever 50 is a closure arm 56 having an upper surface 58 along which a median reinforcement rib 60 extends. A fulcrum portion 62 is disposed between the arm 52 and the arm 56 such that the overall shape of the lever 50 is substantially V-shaped. An end portion 64 of the closure arm 56 is adapted to receive a stopper member 66. Three spaced apart locator flanges 68 *a, b* and c are provided on the end portion 64 and define there between a cavity for receipt of the stopper member 66. Stopper member 66 is composed of a biodegradable EPMD type of synthetic rubber, and is affixed to end portion 64 by means of a biodegradable adhesive, such as PVOH, which is commonly used in many conventional adhesive systems. A pair of high performance, biodegradable thermoplastics torsion spring arms 70, 72 are integrally molded with the base plate 14. Outer ends of the torsion spring arms 70, 72 are connected to the ran flange 36 and the arms 70, 72 extend inward to merge with the fulcrum portion 62 of the lever 50. Thus, the arms 70, 72 and the lever 50 are suspended between the rim flange 36 at a rearward portion of the base plate 14 with the forward closure arm 56 residing with clearance within opening 44 and the trigger arm 52 projecting rearward and upward (as viewed in FIG. 4) from the main body of the base plate 14. The trigger arm 52 is downwardly concave as formed.

Referring next to FIGS. 1, 2, 3, and 5, the handle 16 comprises the handle grip 20 and an internal fluid reservoir 76. A forward, oval shaped, nose portion 78 of the handle 16 is provided having a generally planar, downwardly facing, mounting surface 80 and a domed upper contoured surface 82. A nose flange 84 extends forward from the nose portion 78 in the manner shown. Disposed to extend into opposite sides of the nose portion 78 are a pair of locking depressions 86, 88, each depression providing a horizontal ledge 90 therein. A centrally disposed circular depression 92 extends into planar surface 80, and a central raised circular platform 94 resides within depression 92 terminating at a top surface 96. A circular shoulder 98, best viewed in FIG. 5 circumscribes top surface 96. A passageway 100 is molded to extend through the nose portion surface 80 and communicates with the internal reservoir 76. The underside of the handle 16 is formed to have a concave, elongate depression 102 extending up the handle grip 20; a spring receiving channel 106 extending into and across a rearward portion of the surface 80; and a rib-receiving channel 108 extending into surface 80, commencing at the spring receiving channel 106 and from there on extending forward to the central depression 92.

From a combined consideration of FIGS. 1, 3 4, 5, and 6, it will be appreciated that manufacture and assembly of the subject applicator device is as follows. The sponge member 12 is independently formed of cellulose or Plastarch material. In addition, other applicator surfaces may be utilized within the scope of the present invention. For example, a plurality of brush bristles may be affixed to the underside of base plate 14 if so desired. The sponge 12, in the preferred embodiment, is attached by heat fusion to the base plate 14 underside, and resides within cavity 41, secured to lowermost edge 45 and the lower edges of reinforcement ribs 43 The base plate 14 is formed in include an integral valve, represented by the actuation lever 50, the stopper 66 and the torsion springs 70, 71; 70, 72. The aforementioned components, which comprise the valve, are integrally formed with the body of the base plate 14 of the same material and by the same process.

Figure 5:
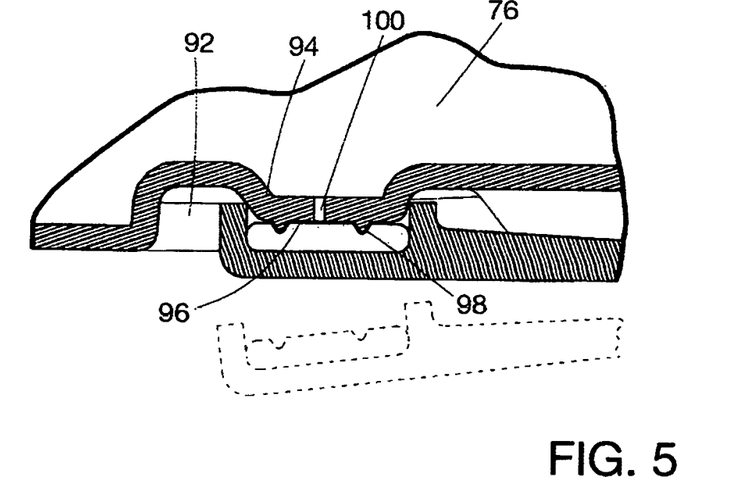
FIG. 5 is an exploded perspective view of the applicator attachment base plate and stopper pad.

As best seen in FIGS. 4 and 5, the stopper 66 is affixed by a suitable biodegradable commercially available adhesive to the stopper end portion 64 of the lever closure arm 56, between protruding flanges 68*a*, band c. The base plate 14 attaches to the nose portion 78 of the handle 16. Nose flange 84 fits within opening 74 of the base plate 14 and is captured. Thereafter, surface 80 is moved downward between plate rim flange 36 and against surface 32. Aligned locking arms, or flanges, 36, 42, align with the depressions 86, 88, respectively, of nose portion 78 of handle 16 and the locking lip 43 of each rides over the locking ledge 90 within each depression 86, 88 to releasably attach the base plate 14 to the handle nose portion 78. The locking arms 36, 40, being formed as cantilevers of plastic material, resiliently flex outward to ride up and over the depression locking ledges 90 during attachment, and flex outward under manual influence to disengage the locking lip 43 from its respective ledge 90, whereby allowing the base plate 14 to separate from the handle nose portion 78. In the attached position, the rib 60 of the lever 50 resides within channel 108 of the nose portion 78; the torsion springs 70, 71; 70, 72 and fulcrum portion 62 reside with the transverse channel 106; and lever trigger arm 50 resides within channel 102. Moreover, in the attached position, the stopper 66 aligns opposite and seats within the depression 92 of the handle nose portion 78 and, therein, engages against the top surface 96. As the stopper 66 bears upon the circular shoulder 98 as shown in FIG. 5, it creates a liquid tight seal there against, whereby blocking water boil from escaping from reservoir 76 by passage 100. The torsion spring members 70, 72 are in a quiescent, or unloaded, state when the stopper 66 in a closed relationship against surface 96. Resistance provided by the torsion spring members 70, 72 to loading acts to maintain the liquid tight seal between the stopper 66 and surface 96. The load required to open the lever 50 is manually applied by digitally pressuring the trigger portion 52 toward handle grip 20, causing pivoting of the lever 50 about fulcrum 62 and closure arm 56 to pivot away from the handle nose portion 78. Such pivotal movement lifts the stopper 66 away from surface 96 and breaks the seal, allowing water boil to escape reservoir 76 through passageway 100. The escaping water boil flows downward about the closure arm 56, through U-shaped opening 44 in the base plate 14, and onto the back side of the sponge 12. From there it is distributed throughout the sponge and onto a surface against which the sponge 12 is pressed. It will be noted that water boil and elective "green" liquids within handle 16, is dispensed at will by pressing the exposed rearward trigger portion 52 of the lever toward the protective handle grip 20. When the lever is pressed towards the handle, the opposite end of the lever 50, arm 56, moves away from the handle, exposing passageway 100 and allowing water boil into the sponge.

Once the desired quantity of water boil is dispensed, and the lever trigger portion 52 is released, the lever 50 will spring back to the closed position. The load required to open the lever, and the automatic closing of the valve is caused by the two torsion springs 70, 72 located on either side of the lever fulcrum portion 62. The springs 70, 72 are substantially cylindrical, of circular cross-section. Outward ends of the spring members 70, 70 are integrally formed with sides of the base plate. Accordingly, the lever, torsion springs, and the base plate are a continuous, integrally formed piece of plastic. The normal, quiescent state of the torsion springs is when the lever is in the closed position. When pivoted into the open position, the lever 50 causes the torsion springs 70, 72 to undergo a moment loading. Potential energy is stored in the torsion springs until the lever arm 52 is released, the energy is released to cause a reverse pivoting of the lever 50 and stopper 66 reassumes a sealing engagement against the nose portion of the arm. The sustainable sponge 12, in various textures, from highly abrasive to gentle cleansing cellulose, can be sold separately as a replacement attachment.

Figures 6, 6A:
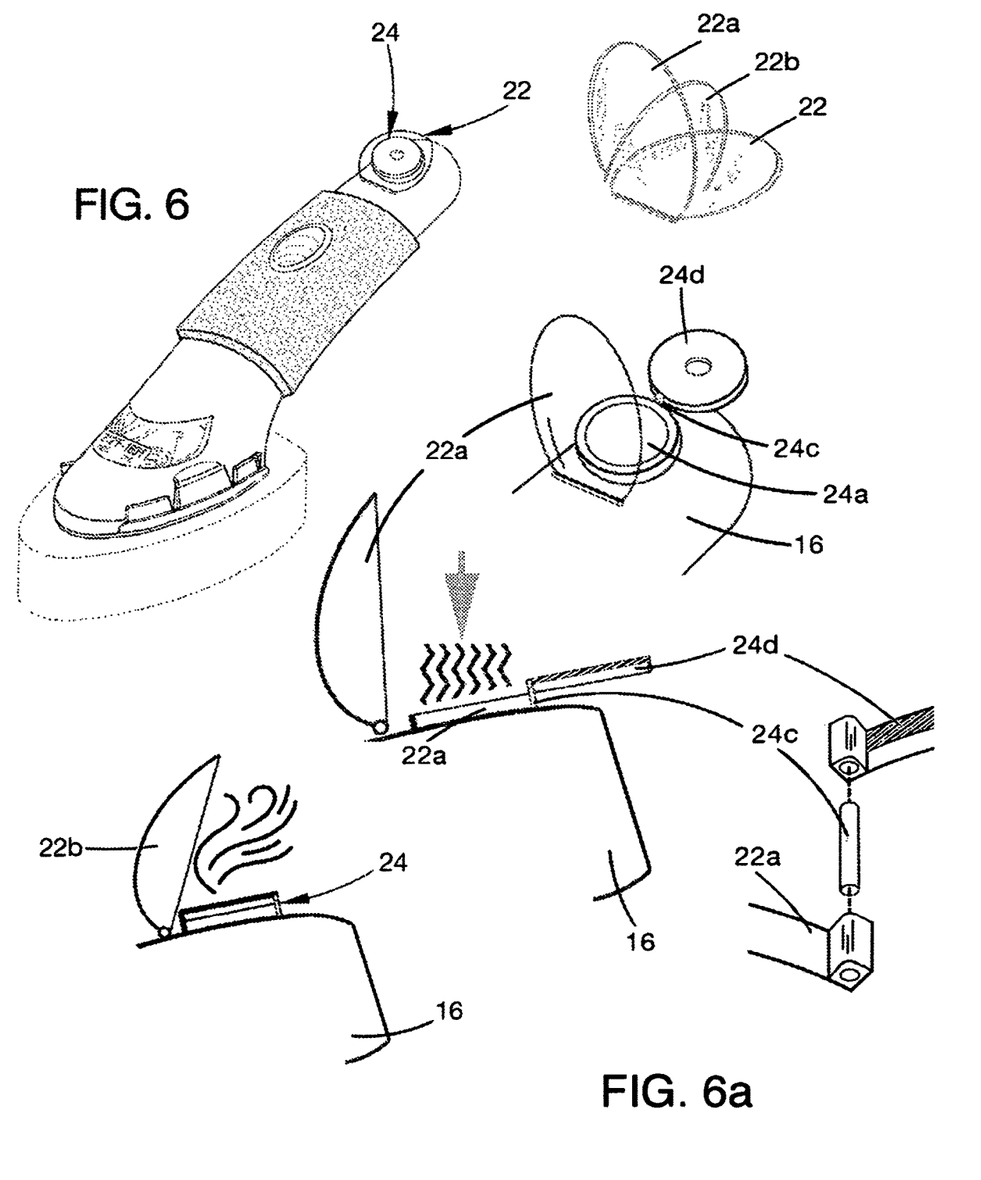
FIG. 6 is a top front view of the subject water boil device protective shield and hole tone.
FIG. 6a is a series of views of the protective shield and hole tone.

Referring to FIGS. 6 and 6a, as FIG. 6 depicts the microwavable handle device, whereas, for the of sake of brevity, the components that comprise the device as enumerated in FIG. 1, are not reprised in this reference, albeit with the exception of the water intake spout 24 and the steam protective shield 22, 22a and *b*, as these components relate to FIG. 6a, as follows: The steam protective shield 22 comprises three distinct positions, 22, 22a and 22b, as each position is actuated by a live hinge manufactured of transparent Plastarch plastic in an injection molding operation that creates all three sections at the same time to create a single part. The fully opened position 22a permits access to the water intake spout 24a through which water enters the reservoir of the handle member 16. The midpoint position 22b shields that portion of the user that may be exposed to steam emitted from steam disc hole 24b of the water intake spout, which is depicted in its closed position 22. The water intake spout, steam escape disc hole, and hinge 24, 24a, 24b, and pin 24c, are manufactured in an injection molding operation of material such as opaque Plastarch plastic with heat-resistant properties, in which the water intake spout 24a and pivoting steam hole disc 24b normally close the end of the spout attached to the base 24a to define an upward passage for alignment in which the pin 24c diameter relative to the openings will be such that the desired pivoting movement is readily obtained.

Figure 7:
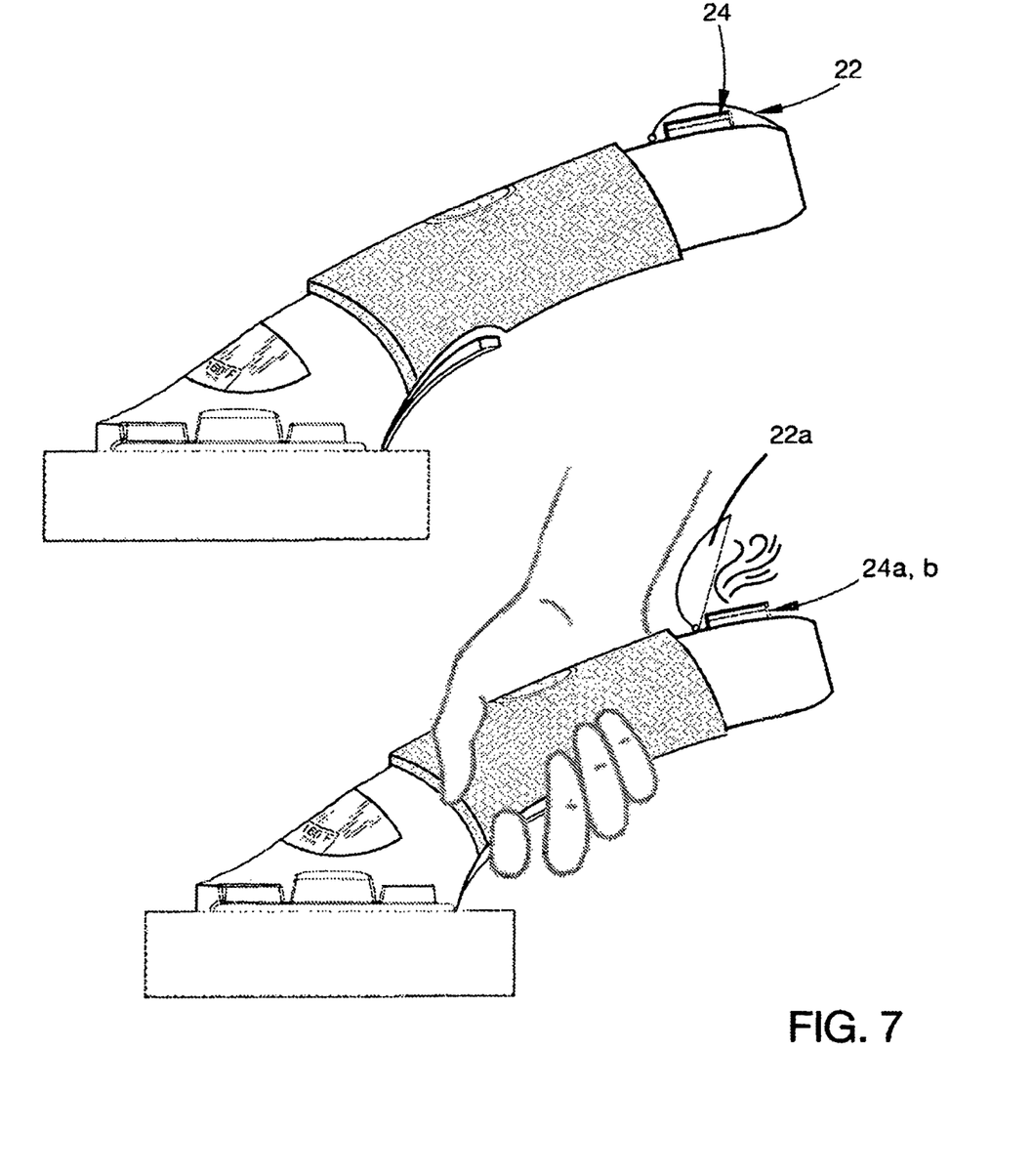
FIG. 7 is a side view of the subject water boil device and operational protective shield.

Referring to FIG. 7, the subject dispensing microwavable device 10 depicts the steam protective shield 22 in its closed position, and, additionally, steam escape from the reservoir 76 through the water intake spout 24a and the steam escape disc hole tone 24d. The present invention is depicted in use and unconnected from its power source, and as such, the protective shield position 22a redirects light steam away from user contact that may occur during normal operation.

Figure 8:
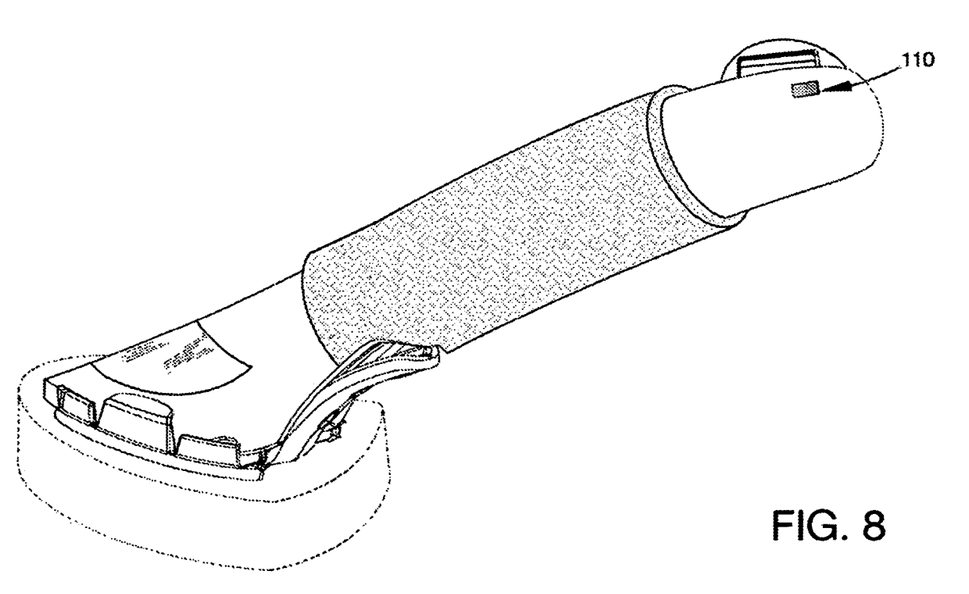
FIG. 8 is a side perspective view of the subject battery operated device and toggle switch.
Figures 9, 10, 11:
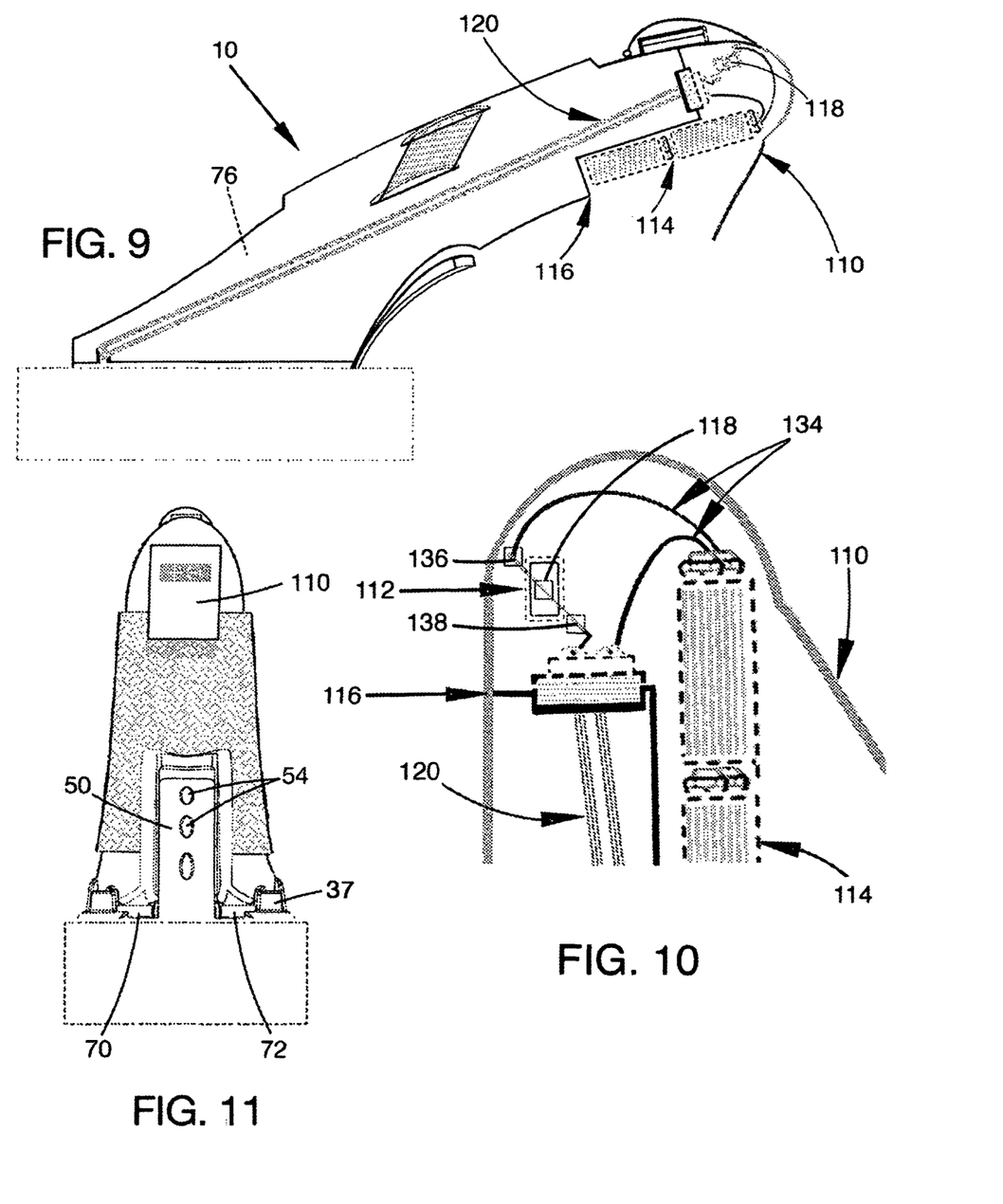
FIG. 9 is an exploded view of the battery device, conventional wiring, and heating element.
FIG. 10 is an exploded view of the battery conventional wiring elements, the compartment, and battery cover.
FIG. 11 is a rear elevation view of the battery operated device, with open battery cover.

Referring to FIG. 8 which depicts a conventional toggle switch 110 for the battery heated water boil iteration of the present handle invention; whereas, for the sake of brevity FIGS. 1, 2 and 2a of the microwavable device apply to FIG. 8, excluding the roughened nucleate interior 28 of the exploded reservoir view 76. In addition, FIGS. 3-5; FIGS. 6, 6a and 7; FIGS. 9-11 apply to the handle device of the battery heated water boil iteration FIG. 8.

Referring next to FIGS. 9-11 the battery powered water boil handle device FIG. 9 exploded view 10 and internal water reservoir 76; a modified conventional immersion water heating element 120; two rechargeable batteries 114; the waterproof battery circuitry compartment (open) 116 and battery and conventional wiring elements compartment cover (open) 110; the switch handle 118, FIG. 10 illustrates a detail of the batteries 114 electron flow wiring of incoming battery power 125 to the immersion water heating element 120; whereas a strip of metal 136 makes contact at 138 and completes the circuit and thereby conducts power to the immersion water heating element 120; thereby constituting the power 'on' position. When the toggle switch 118 is moved in the opposite 'off' position, it pushes the metal strip 126 away from 127, which breaks the circuit and turns the power 'off'. FIG. 11 depicts battery compartment cover (open) 110; the actuation lever 50. The digit-locating protrusions 54 as spaced along an underside of the trigger arm. Outer ends of the torsion spring arms 70, 72 are connected to the rim flange 36. For the of sake of brevity, the detailed explanations expressed in FIGS. 1, 2 and 2a, FIGS. 3-5, and FIGS. 6, 6a and 7 apply, as previous noted regarding components of the present handle invention, to FIGS. 9-11.

Figure 12:
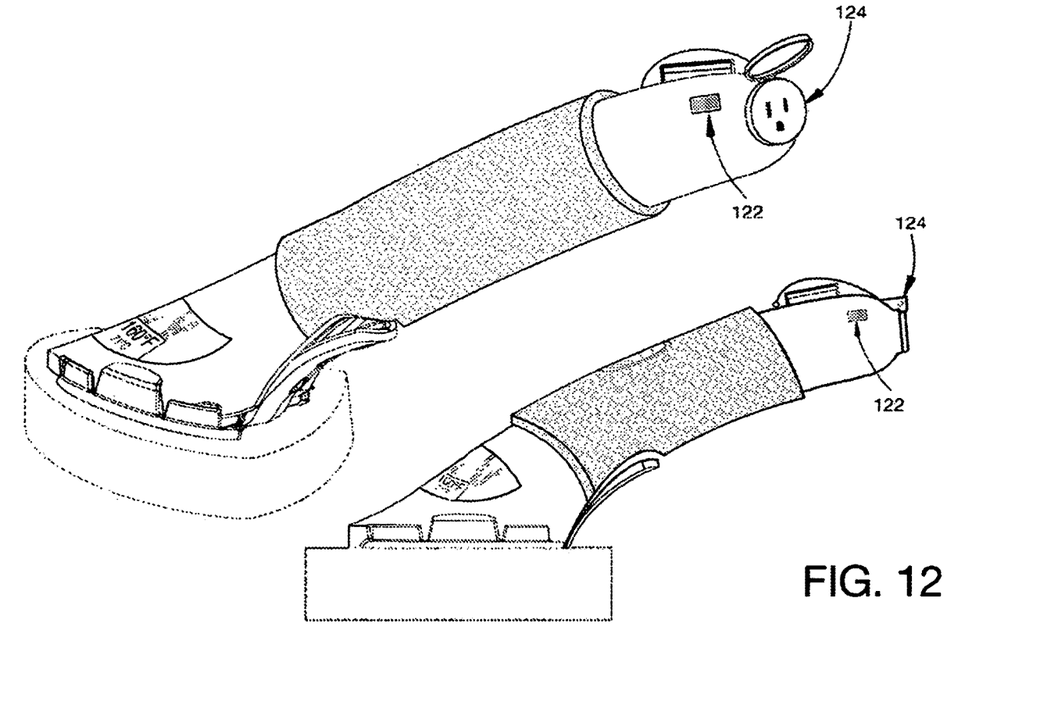
FIG. 12 is a perspective and side view of the subject electrical device, with open and closed sockets.
Figure 13:
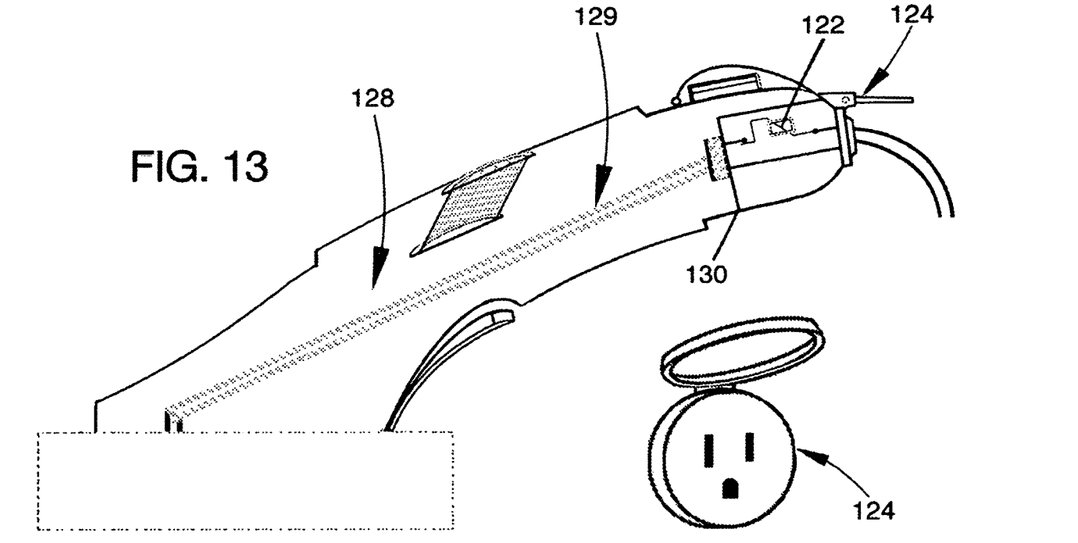
FIG. 13 is an exploded view of the electrical device, conventional wiring elements.
Figure 14:
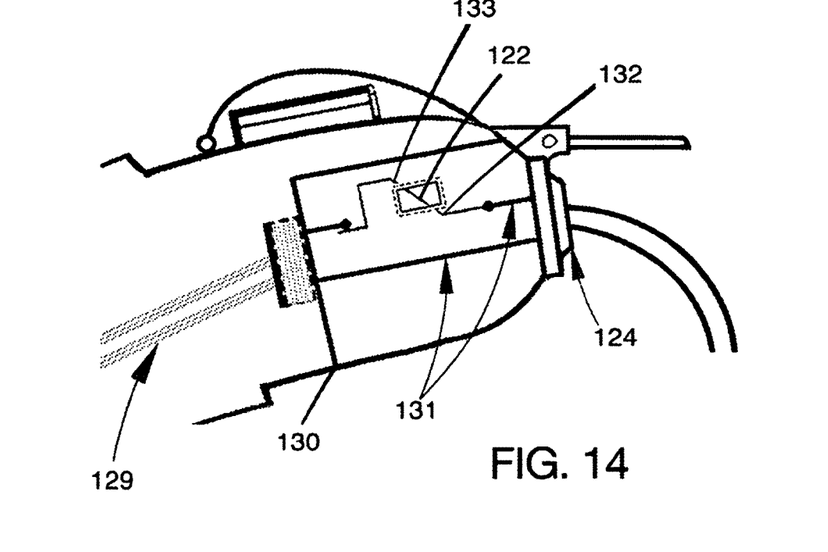
FIG. 14 is an exploded view of the electrical device, conventional wiring detail, and waterproof electrical circuitry compartment.
Figures 15, 16:
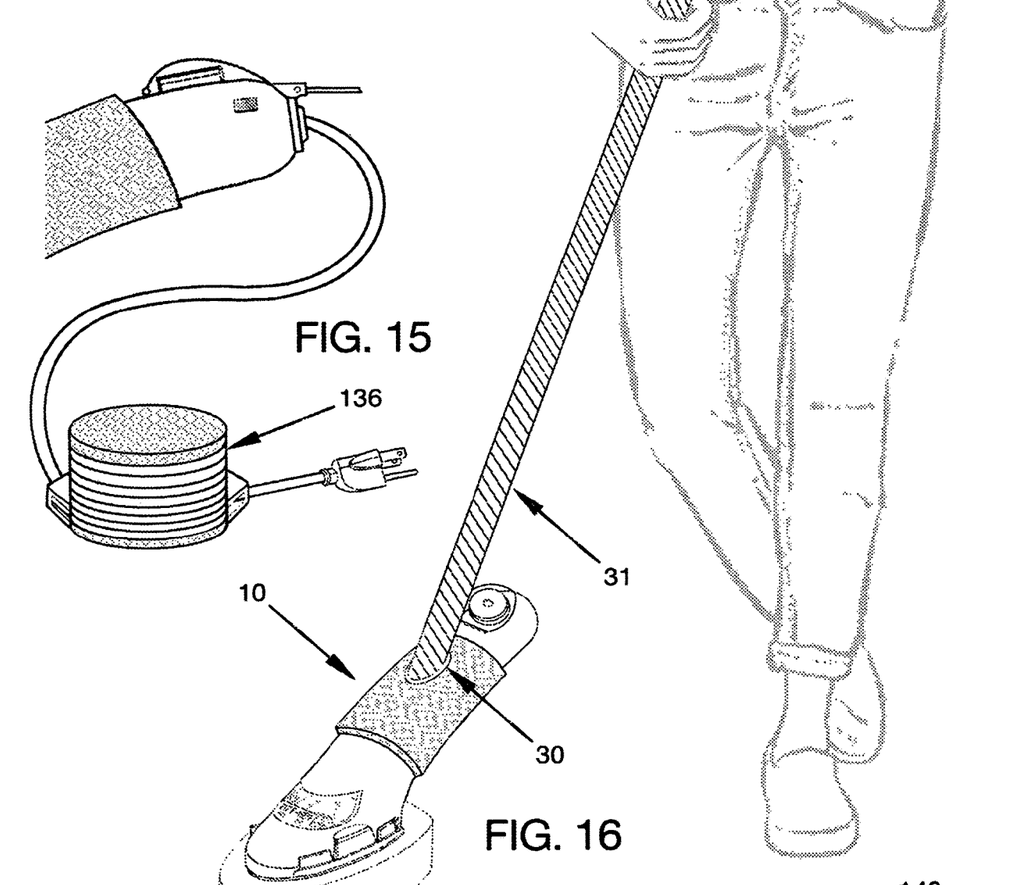
FIG. 15 is a side detail of the electrical device, with an optional electrical cord reel.
FIG. 16 is a top front perspective of the water boil device with optional pole handle extension.
Figure 17:
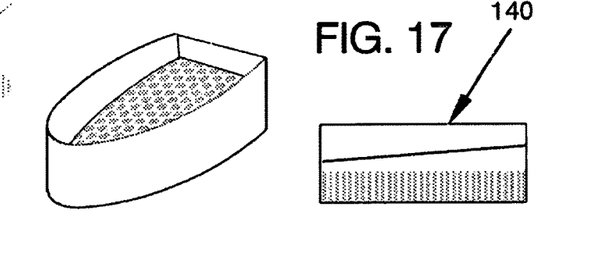
FIG. 17 is a top front perspective and exploded side view of the optional water boil extraction caddy.

Referring next to FIGS. 12-14. FIG. 12 depicts a conventional insulated toggle switch 122 for the electrical iteration, and a conventional weatherproof electrical socket 124. In the interest of concision, the detailed explanations in FIGS. 1, 2, 2a, FIGS. 3-5, and FIGS. 6, 6a, and 7 apply to FIGS. 12-14, excluding, in FIG. 2, the microwavable roughened nucleate interior 28 of the exploded reservoir view 76. FIG. 13 depicts the exploded reservoir view of the electrical iteration 128 in which the water boil is achieved by the immersion water heating element 129 as incoming current at socket 124 is initiated by the "on" position of toggle switch 122. As best seen in FIG. 14, the conventional wiring scheme inside the waterproof electrical circuitry compartment 130, wherein the incoming electrical current 131 makes contact with strip of metal 132 which completes the circuit with metal strip 133 and thereby conducts electricity to the immersion water heating element 129, as the toggle switch would be in the 'on' position. When steam and/or a whistling sound is emitted from the raised safety shield FIG. 6 22a, signaling the consumer that the water boil has been reached, the toggle switch is moved down to the 'off' position, which pushes the metal strip away from 133, breaking the circuit and turning the water heating element off FIGS. 15-17 regard additional cleaning and disinfecting options that may be purchased separately. FIG. 15 depicts a side view detail of the electrical water boil device and conventional electrical cord reel 136. FIG. 16 is a top front perspective of the water boil device with optional pole handle extension 31. FIG. 17 depicts a top front view of a water boil extraction caddy which prompts the user to insert the sponge end member into the caddy and exert downward pressure to release soiled water into the exploded side view of caddy 140, illustrating the inclined platform and water collected beneath it.

What is claimed:

1. A cleaning liquid dispensing implement for dispensing a cleaning liquid, wherein the improvement comprises a cleaning and disinfecting device for dispensing a water boil, and a handle housing having a water spout and hole-tone assembly configured to intake water to an internal connected reservoir, wherein said reservoir comprises means to facilitate the boiling of said water and thereby and emit steam and sound to indicate the said water boil; and wherein a discharge opening through the housing in communication with the reservoir through which said water boil is discharged; an applicator member releasably affixed to said handle housing adjacent said discharge opening, said applicator member comprising a base plate and an applicator element disposed at one side of the base plate; said applicator member further comprising a valve member mounted to said base plate for selectively opening and closing said discharge opening of said handle housing for dispensing the water boil; wherein said valve member includes an actuation member, a stopper member moveable by the actuation member between an open position away from the discharge opening and a closed position in sealing engagement with the handle housing discharge opening, and a biasing member for biasing the stopper member in the closed position; wherein the actuation member includes a lever having a first arm, a second arm extending non-parallel to the first arm, and a fulcrum portion disposed between the first arm and the second arm, and the fulcrum portion is pivotally attached to a lever support portion of the applicator member base plate; wherein selectively opening and closing said discharge opening of said handle housing for dispensing the water boil; whereby said discharge is regulated on stable water boil surfaces; whereas a handle grip surface of said handle housing comprises a protective heat resistant fiber.

2. A cleaning liquid dispensing implement for dispensing a cleaning liquid of claim 1, whereby the temperature range of said water boil disinfects 99.9 percent pathogens on water boil stable surfaces.

3. A cleaning liquid dispensing implement for dispensing a cleaning liquid of claim 1, wherein said device is microwaved, in its entirety, in a conventional microwave oven, whereby said microwave brings said water to said water boil.

4. A cleaning liquid dispensing implement for dispensing a cleaning liquid of claim 1, wherein said microwavable handle housing reservoir of said device is comprised of a roughened interior surface and a non-metallic element, wherein said surface and element create the formation of nucleation sites to prevent a super-heating of said water boil.

5. A cleaning liquid dispensing implement for dispensing a cleaning liquid of claim 1, wherein a plurality of power sources prepare a water boil in said device; wherein said handle housing having said water spout and hole tone assembly configured to intake water to said connected internal reservoir and an external electric current toggle switch on the handle housing is turned to the 'on' position whereby an immersion heating element unit in said reservoir brings said water to a water boil through an external electric current from an electrical conductor internal waterproof handle housing circuitry compartment; emit steam and sound to indicate said water boil; to said reservoir and an external electric current toggle switch on the handle housing is turned to the 'on' position whereby an immersion heating element unit in said reservoir brings said water to a water boil through an external electric current from an electrical conductor internal waterproof handle housing circuitry compartment; wherein said water spout and said hole tone assembly emit steam and sound to indicate the water boil, wherein said external electric current toggle switch is turned to the 'off' position.

6. A cleaning liquid dispensing implement for dispensing a cleaning liquid of claim 1, wherein a plurality of power sources prepare a water boil in said device; wherein said handle housing having said water spout and hole tone assembly configured to intake water to said connected internal reservoir and an external battery current toggle switch on the handle housing is turned to the 'on' position whereby an immersion heating element unit in said reservoir brings said water to a water boil through an internal battery current from a conductor internal waterproof handle housing circuitry compartment; wherein said water spout and hole tone assembly emit steam and sound to indicate the water boil, wherein said external battery current toggle switch is turned to the 'off' position.

7. A cleaning liquid dispensing implement for dispensing a cleaning liquid of claim 1, wherein a plurality of mechanisms control the immersion heating element unit in a handle housing reservoir; whereby a bimetallic thermostat automatically switches off an immersion heating element unit when water reaches a water boil; whereby an electronic thermostat repeatedly switches an immersion heating element unit on and off to maintain the water boil temperature.

8. A cleaning liquid dispensing implement for dispensing a cleaning liquid of claim 1, wherein each of said plurality of power sources have a steam safety shield adjacent said water intake spout and hole tone assembly from which steam escapes when water within the reservoir reaches a boil; wherein said escaping steam indicates that the water boil is prepared for use; wherein said steam safety shield protects against steam emanating from said device during cleaning and disinfecting process.

9. A cleaning liquid dispensing implement for dispensing a cleaning liquid of claim 1, wherein said plurality of power sources prepare the water boil, wherein a modicum of biodegradable water boil soap concentrate is added, as a user elective, to said reservoir through said water intake spout.

10. A cleaning liquid dispensing implement for dispensing a cleaning liquid of claim 1, wherein the base plate includes a pair of projections configured to releasably affix the applicator member to the handle housing; wherein said biasing member includes a torsion spring that merges with the fulcrum portion; wherein said plate member releasably attachable to a handle housing and an applicator element disposed at one side of the base plate, the improvement comprising: a valve member mounted to said base plate said mechanism for selectively opening and closing a discharge of said water boil opening in said handle housing for dispensing the water boil, said valve member including said actuation member, said stopper member moveable by the actuation member between an open position away from the discharge opening, and a biasing member for biasing the stopper member in the closed position; wherein the actuation member including said lever having a first arm, a second arm extending non-parallel to the first arm, and said fulcrum portion disposed between the first arm and the second arm, and the fulcrum portion is pivotally attached to said lever support portion of the applicator base plate.

11. A cleaning liquid dispensing implement for dispensing a cleaning liquid of claim 1, said valve member and said base plate being formed as an integral one piece unit; wherein said stopper member is attached to a remote end of said lever first arm; wherein a second lever arm pivots toward and away from said handle housing, whereby moving said stopper member between said closed and said open positions.

12. A cleaning liquid dispensing implement for dispensing a cleaning liquid of claim 1, wherein second lever arm pivots toward and away from said handle housing, whereby moving said stopper member between said closed and said open positions; wherein said lever support portion of said applicator base plate comprises a torsion spring.

13. A cleaning liquid dispensing implement for dispensing a cleaning liquid of claim 1, wherein said biasing member comprises said torsion spring, whereby said torsion spring comprises a transversely extending torsion arm integrally formed with the base plate member at opposite first and second ends and supporting said lever fulcrum portion at a mid-portion between said first and second torsion arm ends.

14. A cleaning liquid dispensing implement for dispensing a cleaning liquid of claim 1, wherein said actuation member together with said biasing member and said applicator baseplate being formed as an integral one-piece unit.

15. A cleaning liquid dispensing implement for dispensing a cleaning liquid of claim 1, wherein a microwavable water boil handle housing device having said water spout, said hole tone, and said reservoir assembly, whereby said assembly facilitates the intake of a water boil prepared externally, by such means as to bring water to a boil.

16. A cleaning and disinfecting water boil dispensing devise comprising: a handle housing having an internal connected reservoir the with means to facilitate the boiling of water and a discharge opening through the housing which is in communication with the reservoir and through which the water boil is discharged; an applicator member releasably affixed to the handle housing adjacent the discharge opening, the applicator member including a base plate, a sponge disposed at one side of the base plate, and a valve member mounted to the base plate for selectively opening and closing the discharge opening of the handle housing for dispensing the water boil; wherein the valve member comprises an actuation member, a stopper member moveable by the actuation member between an open position away from the discharge opening and a closed position in sealing engagement with the handle housing-discharge opening, and a biasing member for biasing the stopper member in the closed position; wherein the actuation member comprising a lever, the lever comprising a first arm, a second arm extending non-parallel to the first arm, and a fulcrum portion disposed between the first arm and the second arm, and the fulcrum portion is pivotally attached to a lever support portion of the applicator member base plate; wherein the biasing member includes a torsion spring that merges with the fulcrum portion.

17. A cleaning and disinfecting water boil dispensing device of claim 6, comprising: the valve member with said actuation member between an open position away from the discharge opening and a closed position in sealing engagement with the handle housing discharge opening, and a biasing member for biasing the stopper member in the closed position; wherein said device safely regulates the discharge of said water boil on stable water boil surfaces.

18. A cleaning and disinfecting water boil dispensing device of claim 16, wherein the stopper member is attached to a remote end of the lever first arm; wherein the second lever arm pivots toward and away from the handle housing, whereby moving the stopper member between the closed and the open positions.

19. An applicator device for dispensing a water boil, comprising: a handle housing having an internal reservoir configured to store the water boil, and a discharge opening said mechanism through the housing in communication with the reservoir through which the water boil is discharged; an applicator member releasably affixed to the handle housing adjacent the discharge opening; the applicator member comprising a base plate and an applicator element disposed at one side of the base plate; the applicator member further comprising a valve member mounted to the base plate; whereby said mechanism selectively opening opens and closing closes the discharge opening of the handle housing for to selectively dispense dispensing the water boil, wherein the valve member comprises an actuation member, a stopper member moveable by the actuation member between an open position away from the discharge opening and a closed position in sealing engagement with the handle housing discharge opening, and a biasing member for biasing the stopper member in the closed position; wherein the actuation member comprising a lever, the lever comprising a first arm, a second arm extending non-parallel to the first arm, and a fulcrum portion disposed between the first arm and the second arm, and the fulcrum portion is pivotally attached to a lever support portion of the applicator member base plate.

20. The applicator device of claim 19, wherein the actuation member comprising a lever, the lever comprising a first arm, a second arm extending non-parallel to the first arm, and a fulcrum portion disposed between the first arm and the second arm, and the fulcrum portion is pivotally attached to a lever support portion of the applicator member base plate.

21. The applicator device of claim 20, wherein the lever support portion of the applicator base plate comprises a torsion spring; wherein the biasing member comprises the torsion spring.

\* \* \* \* \*